United States Patent [19]

Tarrson et al.

[11] Patent Number: 4,925,073
[45] Date of Patent: May 15, 1990

[54] DENTAL FLOSS HOLDER

[75] Inventors: Emanuel B. Tarrson; Dane Maric, both of Chicago, Ill.

[73] Assignee: John O. Butler Company, Chicago, Ill.

[21] Appl. No.: 341,125

[22] Filed: Apr. 20, 1989

[51] Int. Cl.⁵ .................. B26F 3/00; B65H 35/00
[52] U.S. Cl. ........................ 225/44; 225/46; 225/51; 225/77; 242/138
[58] Field of Search ............ 225/44, 45, 46, 48, 225/51, 77; 242/137, 137.1, 138

[56] References Cited

U.S. PATENT DOCUMENTS

| | | | |
|---|---|---|---|
| 1,454,429 | 5/1923 | Dresser | 242/138 |
| 1,455,673 | 5/1923 | Shalek | 242/138 |
| 3,246,815 | 4/1966 | Aronson | 225/44 |
| 4,073,419 | 2/1978 | Tarrson et al. | 225/44 |

Primary Examiner—Hien H. Phan
Attorney, Agent, or Firm—Laff, Whitesel, Conte & Saret

[57] ABSTRACT

A dental floss holder is in the form of a box with a drawer in it. The bottom of the drawer includes a hub which is spring biased to push a bobbin mounted thereon toward an opposite side of the box. The bias is such that the bobbin drags with a predetermined force on an opposite side of the box to maintain tension in the floss. A result is that the bobbin does not unwind while in the holder, thereby precluding a snarled floss line. Also, the tension gives a smooth "pull" which adds a "feel" of quality to the floss. The "feel" does not change as the diameter of the bobbin changes with either an exhaustion of floss or changes in the diameter of a full bobbin. The hub is mounted on a dome having sides with a shape which guides and directs any floss falling off the bobbin back onto it.

20 Claims, 1 Drawing Sheet

U.S. Patent May 15, 1990 4,925,073
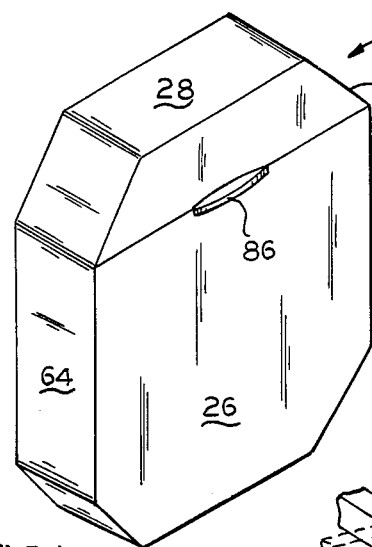
FIG.1
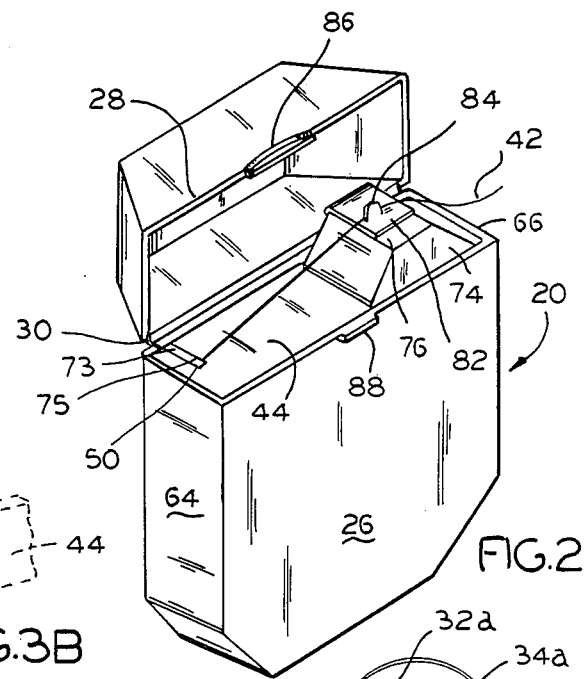
FIG.2
FIG.3B
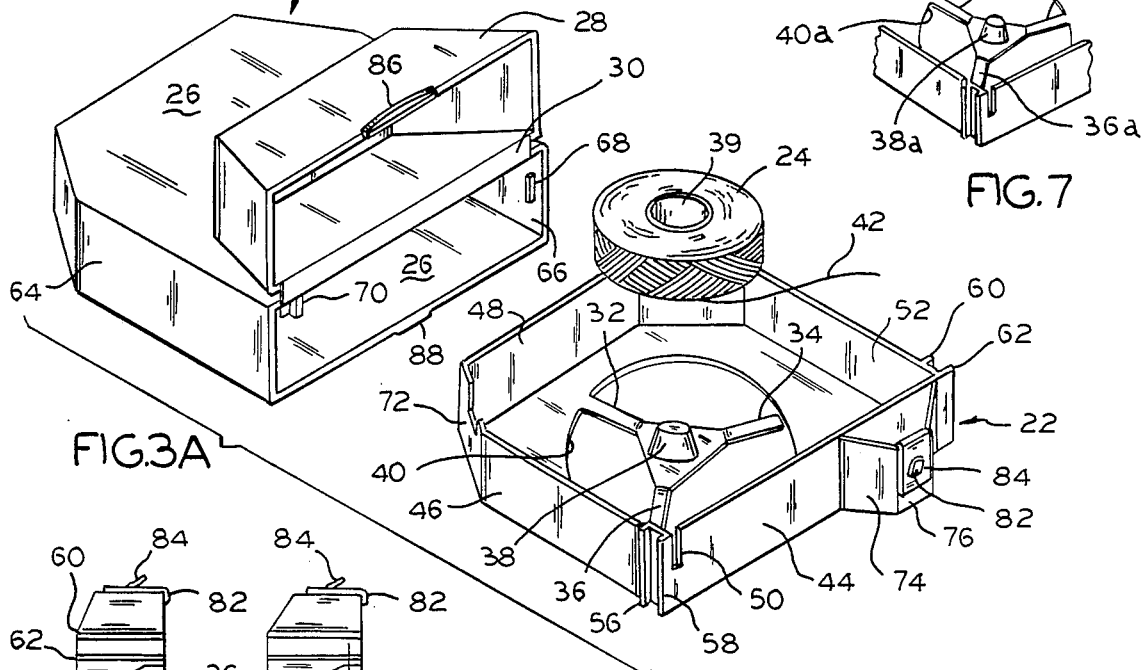
FIG.3A
FIG.7
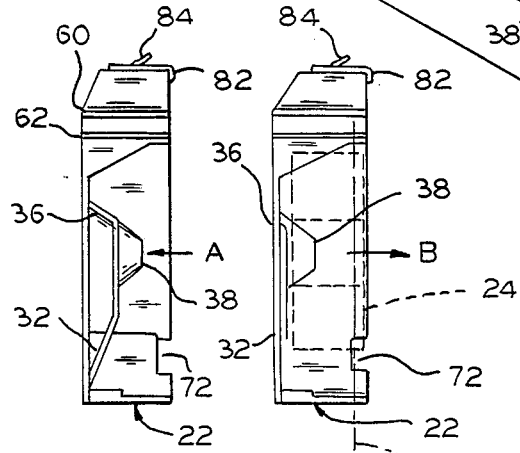
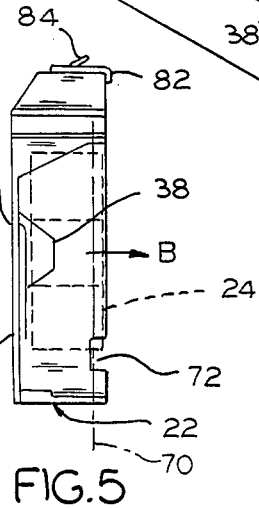
FIG.4  FIG.5
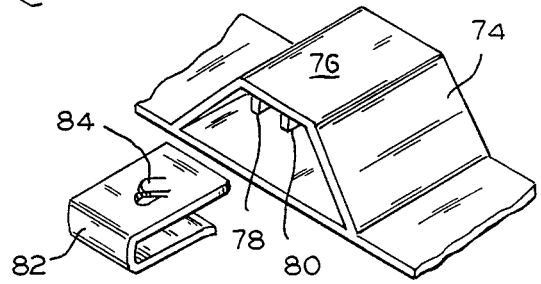
FIG.6

DENTAL FLOSS HOLDER

This invention relates to dental floss holders and more particularly to holders for storing a great variety of different lengths of floss. One example of such a floss holder is found in U.S. Pat. No. 4,073,419.

A dental floss holder should be handy, easy to use, and small enough to be carried in pocket or purse. The floss should not become snarled as it is carried about. When the floss is pulled, there should be a "feel" of quality so that the floss is smoothly delivered with enough resistance or tension to prevent the floss from unwinding or falling off the bobbin within the housing. If, despite the tension, the floss should fall off the bobbin, some means should be provided for redirecting the floss back and onto the bobbin.

Heretofore, there has been a tendency for the "feel" of quality to depend upon how much floss is or remains on the bobbin. When a full bobbin is in place, the braking action which controls the "feel" has depended upon the relatively large amount of friction between the relatively large area at the end of the full bobbin and a nearby interior surface of the floss holder. As the bobbin is exhausted, its diameter becomes progressively smaller so that braking depends upon a progressively smaller area of contact between bobbin and interior surface, producing an ever reducing amount of friction. As a result, there was a noticeable difference in the "feel" at the start and near the end of the floss. In some prior floss holders, there was almost no resistance to the pull of the floss as the last few feet were used.

Holders or dispensers for dental floss must cope with a number of different problems. The holders must have an extremely low cost since they are throw-a-way items for products which sell at a relatively low price. The holders should be readily adapted to be manufactured on completely automatic production machines, where one may simply turn on an unattended machine and produce a steady stream of end products which are packaged and ready to ship to a retailer. Conversely, the holder should also be adapted to easy hand assembly for use by those who either do not have or elect not to use automatic production machinery.

Dental floss holders should be readily adaptable to be used with many different sizes of bobbins so that the same holder may contain any of a variety of different lengths, such as 15, 50 or 100 yards of floss. This is especially important when automatic production machinery has been dedicated to a production of the floss holder and it would be extremely expensive to change a set up each time that a new length of floss is packed in the holder. Again there should not be a noticeable difference in the "feel" as floss is pulled from the bobbin regardless of whether the floss is being pulled from a relatively large and full holder of 100-yards or a relatively small and nearly exhausted holder of 15-yards.

Accordingly, an object of this invention is to provide new and improved dental floss holders. Here, an object is to provide floss holders which lend themselves to both automatic and manual production.

Another object of the invention is to provide floss holders which have a feel of quality as the floss is pulled from the holder. Here an object is to provide a resistance to an unwinding of the bobbin which prevents the floss from becoming snarled in the housing. In particular, an object is to provide a resistance to the pulling of the floss, which is uniform throughout the life of the floss holder and which does not change with the exhaustion of the floss supply.

Yet another object of the invention is to accommodate a great variety of different bobbin sizes without simultaneously making a bobbin housing which is unduly large and clumsy.

In keeping with an aspect of the invention, these and other objects are accomplished by a two piece housing or floss holder assembly. One of the pieces is in the nature of a drawer and the other a shell into which the drawer slides. The bottom of the drawer has a truncated conical dome shaped member which functions both as a hub on which a bobbin of dental floss turns and further which guides and directs the floss back onto the bobbin if it should fall off the bottom of the bobbin. The dome shaped member is supported on a spider of legs which press the bobbin against an opposite wall of the shell with a force that is high enough to prevent a random unwinding of the bobbin and that is low enough to permit an easy turning of the bobbin when the floss is pulled. Above the bobbin, a stepped ridge keeps the floss on the bobbin and closes an opening through which the floss might escape.

A preferred, embodiment of the invention is shown on the attached drawing in which:

FIG. 1 is a perspective view of the inventive dental floss holder in a closed condition, which is the condition in which it may be carried or stored;

FIG. 2 is a similar perspective view with the top opened and with a withdrawn length of dental floss being cut off;

FIG. 3A is an exploded view, in perspective, showing the two holder parts and bobbin of dental floss;

FIG. 3B is a perspective view of an end of a stepped ridge which acts as both a floss retainer and a strengthening rib;

FIG. 4 is a side elevation of the drawer housing part, without a floss bobbin in place;

FIG. 5 is a similar end view, but with a floss bobbin in place and being pressed against the side of the housing shell;

FIG. 6 is a fragmentary view showing a metal clip which includes a tang that may be used to cut the floss and to hold the end of the floss after it is cut; and FIG. 7 shows a second embodiment of a hub element with spoke-like spider legs attached at each of their opposite ends.

The dental floss holder is formed from two parts 20, 22. As best seen in FIG. 3A, part 20 is a box-like shell for receiving and holding part 22, which is in the nature of a drawer contain a bobbin 24 of dental floss. Shell 20 has a pair of side walls 26, 26 with a flip top 28 joined to one of them by a living hinge 30. This entire shell (top and bottom) may be a single piece part molded from plastic.

The drawer 22 is an integrally molded unit which has a large circular opening or hole 40 in the bottom with a spider of legs 32, 34, 36 extending in a spoke-like manner to support a truncated conical dome or hub 38 at the center of hole 40. A central hole 39 in bobbin 24 rests on and turns about dome or hub 38. The hole 39 in the bobbin may be defined by a short section of any suitable tubing, such as cardboard, plastic, or the like without any end flanges. The leg 32 is attached to drawer 22 at a point on the circumference of circular opening 40. The other two legs 34, 36 are not attached at their outer ends, but are free to slide back and forth as the dome is pushed in the direction of the drawer bottom (direction A, FIG. 4).

The legs 32, 34, 36 have a spring-like quality as a result of the memory of the plastic. Thus, the resilience of the legs 32, 34, 36 urge hub 38 into hole 39 formed by the short section of tubing and, therefore, urges the bobbin 24 in direction B (FIG. 5). The tubing is pushed against an opposite side wall 26 of the shell 20. The resulting spring bias applied by legs 32, 34, 36 to the bobbin is adequate to create a tension in the floss which prevents a random unwinding of the floss while permitting the bobbin to turn as dental floss 42 is pulled. Nevertheless, if, despite the tension, the floss should fall off the bottom of the bobbin, the fact that the side wall of the dome is conical means that any floss which does fall off is guided back onto the bobbin and reset into a proper position.

The dome 38 may have any of many different cross sections. For example, in a vertical plane, it may bulge and round out or be depressed and flared. In the horizontal plane, the dome is here shown as having a circular cross section, but other shapes may be used as long as a tension upon the floss causes it to return to the bobbin.

A result is that the smooth "pull" of the floss gives a feel of quality, without any relationship to the size of the bobbin. In greater detail, the dimensions are such that the braking action of dome 38 acts upon the end of the tubing, pressing it against the opposite wall of the housing. Since the dimensions of the tubing do not change with the exhaustion of the floss supply, the resistance to the pull of the floss is practically uniform throughout the life of the floss holder. Also, the resistance does not depend upon the initial amount of the floss so that any of many different sizes of bobbins may be used in the same housing. The resistance continues until the inner end of the floss is no longer gripped against the tubing by the overlying layers of floss wrapping over its end. As a practical matter, this usually means that there is a uniform resistance to the pull upon the floss down to its last inch or two.

The remainder of the drawer construction is primarily designed to give strength and stability. More particularly, the four sides of the drawer includes upstanding walls 44, 46, 48, 52 which give rigidity to the base and stability to the drawer 22 when it is enclosed within the shell 20. Also, wall 44 closes the shell opening to establish and maintain a clean and sanitary interior in the holder. A slot 50 is formed in end wall 44 to give egress for floss 42. Two small ridges 56, 58 and 60, 62 are formed on and near the top of walls 46, 52, to provide a keeper which snaps over opposing embossments in opposite side walls 64, 66 of the housing shell. One of these embossments is seen at 68 (FIG. 3A).

The interior of shell 20 includes a longitudinal, ridge 70 (FIG. 3B) with a stepped end which is integrally formed on a side wall 26 (FIG. 3A) and which extends through out the entire length of the shell 20. Ridge 70 provides four functions, it gives rigidity to the shell, provides a guide rail for drawer 22, holds the drawer side wall 46 tightly against side 64 of shell 20, and closes the slot 50, leaving only a small hole 75 FIG. 3B for floss to leave the housing. The drawer 22 includes a notch 72, through which the ridge 70 passes as the drawer slides within the shell. More particularly, as best seen in FIG. 3B, the rib is relatively thick along its length and then reduces to a flange 73 which fills most of the slot 50, leaving only a small hole 75 through which the floss will escape. Also, the end 73 of the ridge 70 projecting into the slot 50 stabilizes the position of drawer 22 and panel 44.

Upstanding on wall 44 is an integral arched number 74 which includes a flat top 76 (FIG. 6). The underside of arched top 76 includes two strengthening ribs 78, 80. A metal clip 82 slips over top 76 and ribs 78, 80 with a friction which is adequate to hold it in place. The upper surface of clip 82 is cut by a semi-piercing die to make an upstanding tang or tongue 84. When the dental floss 42 is placed under tang 84 and pulled, the floss is cut. The bobbin end of the floss is captured and held under the tang.

The assembly of the parts should now be clear. The bobbin 24 is placed on the hub formed by the truncated conical dome 38. The end 42 of the floss is drawn through slot 50. Then, the drawer 22 is slid into the shell 20. As it reaches the shell 20, the bobbin 24 is pressed down (Direction A, FIG. 4) against the spring bias of legs 32, 34, 36 until the bobbin is low enough to slide into the shell 20. Drawer 22 is pushed further into the shell until the ribs 56–62 snap over embossments, such as 68, on the inside surface of the opposite shell side walls 64, 66. At this time the end fin 73 on stepped ridge 70 fill most of slot 50 to retain the end of the floss in the housing. While it is not necessary, the drawer may then be ultrasonically welded or otherwise bonded in place, if desired. The loose floss end is placed under tang 84 to cut off an extended portion and capture a remaining end of the floss.

The top 28 of shell 20 has a catch 86 (FIG. 2) integrally molded therein. A mating embossment 88 is formed on the upper edge of the shell bottom surface. Therefore, when the top 28 is closed over the bottom, the catch 86 snaps over the embossment 88.

FIG. 1 shows the completed assembly with the top closed. FIG. 2 shows the same assembly with the top 28 open and with the dental floss passed under tang 84.

FIG. 7 shows a second embodiment of a bobbin support that is substantially the same as the support of FIG. 3 which has already been described. The difference is that each of the spoke-like leg members 32a, 34a, 36a of the spider is attached on both ends to the periphery of hole 40a and the hub 38a. The selection between the embodiments of FIG. 3 and FIG. 7 depends primarily upon the memory characteristics of the plastic that is used to construct the part 22.

An advantage of the invention is that the holder is small enough to be acceptable even when a bobbin containing as much as 100-yards of dental floss is enclosed therein. Smaller bobbins may be used in the same housing for holding lesser amounts of dental floss. Accordingly, to change the amount of floss in the holder, it is not necessary to change a production line, except to substitute one bobbin for another. Moreover the amount of resistance to bobbin turning may be controlled much more precisely than heretofore, and independently of the amount of floss remaining on the bobbin. As a result, considering the maximum amount of floss housed therein, the overall size of the holder may be smaller and less expensive than with other prior art holders.

Those who are skilled in the art will readily perceive how to modify the invention. Therefore, the appended claims are to be construed to cover all equivalent structures which fall within the true scope and spirit of the invention.

The claimed invention is:

1. A dental floss holder comprising a drawer and a shell into which said drawer slides with a fairly snug fit, said drawer being an integral plastic unit with bottom surface having a spider supporting a centrally located hub element inside said drawer, said plastic having a memory which gives said spider a spring bias for urging said hub toward an opposite side of said shell, and a bobbin of dental floss mounted on said hub, said hub having length which causes said bobbin to drag under said spring bias against an opposite side of said shell with a force which maintains a predetermined tension in said dental floss.

2. The dental floss holder of claim 1 wherein said spider comprises at least three spoke-like members, one of which is attached on both ends extending between said hub and said drawer, the other of said spoke-like members being attached on only one end and extending between said hub and said drawer, the unattached ends of said other spoke-like members being free to slide as said bobbin is pressed against said hub and said spring bias increases.

3. The dental floss holder of claim 1 wherein said shell has an internal longitudinal ridge extending throughout the length of said shell and extending parallel to a path followed by said drawer as it slides into said shell, and means on said drawer for cooperating with said longitudinal ridge for stabilizing the position of said drawer with respect to said shell.

4. The dental floss holder of claim 3 wherein said cooperating means is a slot in said drawer, and said ridge is a stepped ridge with an end flange which fills most of said slot leaving a small hole through which said floss emerges from said housing whereby said ridge prevents said floss from snarling or coming out of said slot.

5. The dental floss holder of claim 1 wherein said shell has a bottom part with a flip-top part attached thereto by a living hinge, and means formed on said shell bottom part and said flip-top part for latching said top to said bottom when said top is closed.

6. The dental floss holder of claim 1 and means for latching said drawer to said shell after said drawer has slid to a completely closed position.

7. The dental floss holder of claim 6 wherein said drawer is bonded into said shell when said drawer is in said completely closed and latched position.

8. The dental floss holder of claim 1 wherein the amount of said drag is independent of the amount of floss that is on said bobbin.

9. The dental floss holder of claim 1 wherein said bobbin comprises floss wound on a tube, the length of said tube providing said length of said hub, said centrally located hub fitting into and applying a predetermined amount of friction to said tube.

10. The dental floss holder of claim 1 wherein said spider comprises at least three spoke-like members, each of which members being attached on both ends and extends between said hub and said drawer in order to urge said bobbin against said opposite side of said shell in response to said spring bias.

11. A dental floss holder comprising a box with a bottom part having a flip-top part hinged thereto, a drawer for sliding into said bottom part of said box, means associated with said box and with said drawer for forming a hole through which floss may emerge from said box and for securing said drawer in said bottom part of said box with very little play, an opening on the bottom of said drawer, a plurality of resilient spoke-like elements positioned within said opening for supporting a hub element, said spoke-like elements applying to said hub element a spring bias acting in a direction from the bottom of said drawer toward an opposite side of said box, and a bobbin rotatably supported by said hub element, said bobbin having a thickness which causes it to drag under said spring bias with a predetermined force against an opposite side of said box.

12. The holder of claim 11 and a cutter on a surface of said drawer which is covered by said flip-top when said top part is closed over said bottom part of said box.

13. The holder of claim 12 and ribs on at least two side walls of said drawer for snapping over an embossment in said box to hold said drawer in a closed position.

14. The holder of claim 13 and means for bonding said drawer in a closed position.

15. The box of claim 13 and a guide rail on an internal surface of said box for guiding said drawer as it slides and for capturing and holding said box in a stable position with respect to at least one side walls of said drawer.

16. The box of claim 13 and an arch formed on a surface of said drawer which is covered by said flip-top, a metal clip shaped to slip over and grip said arch, said metal clip having a tang formed therein to provide said cutter.

17. The holder of claim 16 and at least one rib formed on said arch for providing strength and stability to hold said metal clip.

18. The box of claim 11 wherein said means for forming said hole comprises a stepped guide rail on an internal surface of said box for closing most of a slot in a side wall of said drawer, said hole being formed at the root of said slot after said most of said slot is closed.

19. The holder of claim 11 wherein one of said spoke-like members is attached to a periphery of said opening and the remainder of said spoke-like members are unattached at one end so that they are free to slide as said bobbin applies a force to urge said hub to resist said spring bias.

20. The holder of claim 11 wherein each of said spoke-like members extends between and is attached to a periphery of said opening and the hub element in order to apply a force to urge said hub to resist said spring bias.

* * * * *